(12) United States Patent
Kawana et al.

(10) Patent No.: US 9,815,826 B2
(45) Date of Patent: Nov. 14, 2017

(54) CRYSTAL OF AZOLE BENZENE DERIVATIVE

(71) Applicant: TEIJIN PHARMA LIMITED, Tokyo (JP)

(72) Inventors: Asahi Kawana, Tokyo (JP); Yuki Miyazawa, Tokyo (JP)

(73) Assignee: Teijin Pharma Limited, Chiyoda-ku, Tokyo (JP)

( * ) Notice: Subject to any disclaimer, the term of this patent is extended or adjusted under 35 U.S.C. 154(b) by 0 days.

(21) Appl. No.: 15/328,146

(22) PCT Filed: Jul. 29, 2015

(86) PCT No.: PCT/JP2015/071512
§ 371 (c)(1),
(2) Date: Jan. 23, 2017

(87) PCT Pub. No.: WO2019/017696
PCT Pub. Date: Feb. 4, 2016

(65) Prior Publication Data
US 2017/0210735 A1   Jul. 27, 2017

(30) Foreign Application Priority Data
Jul. 30, 2014   (JP) .................................. 2014-155031

(51) Int. Cl.
*C07D 417/10*   (2006.01)
(52) U.S. Cl.
CPC ........ *C07D 417/10* (2013.01); *C07B 2200/13* (2013.01)
(58) Field of Classification Search
CPC .................................................. C07D 417/10
USPC ............................................................ 514/365
See application file for complete search history.

(56) References Cited

U.S. PATENT DOCUMENTS

| 5,843,969 | A | 12/1998 | Ota et al. |
| 9,388,174 | B2 * | 7/2016 | Kawana ............... C07D 417/10 |
| 2009/0306396 | A1 | 12/2009 | Toyoshima et al. |
| 2010/0227864 | A1 | 9/2010 | Shimizu et al. |

FOREIGN PATENT DOCUMENTS

| EP | 0 513 379 A1 | 11/1992 |
| WO | 96/31211 A1 | 10/1996 |
| WO | 2007/043400 A1 | 4/2007 |
| WO | 2008/126770 A1 | 10/2008 |
| WO | 2008/126899 A1 | 10/2008 |
| WO | 2014/119681 A1 | 8/2014 |
| WO | WO2014119681 A1 * | 8/2014 ............. C07D 17/10 |

OTHER PUBLICATIONS

International Search Report for PCT/JP2015/071512 dated Sep. 15, 2015 [PCT/ISA/210].
Written Opinion for PCT/JP2015/071512 dated Sep. 15, 2015 [PCT/ISA/237].
Communication dated Apr. 4, 2017 from the European Patent Office in counterpart Application No. 15827012.4.

* cited by examiner

*Primary Examiner* — Yong Chu
(74) *Attorney, Agent, or Firm* — Sughrue Mion, PLLC

(57) ABSTRACT

There are provided crystals of 2-[4-(2,2-dimethylpropoxy)-3-(1H-1,2,3,4-tetrazol-1-yl)phenyl]-4-methyl-1,3-thiazole-5-carboxylic acid which is useful as a therapeutic agent or prophylactic agent for gout, hyperuricemia and the like.

4 Claims, 1 Drawing Sheet

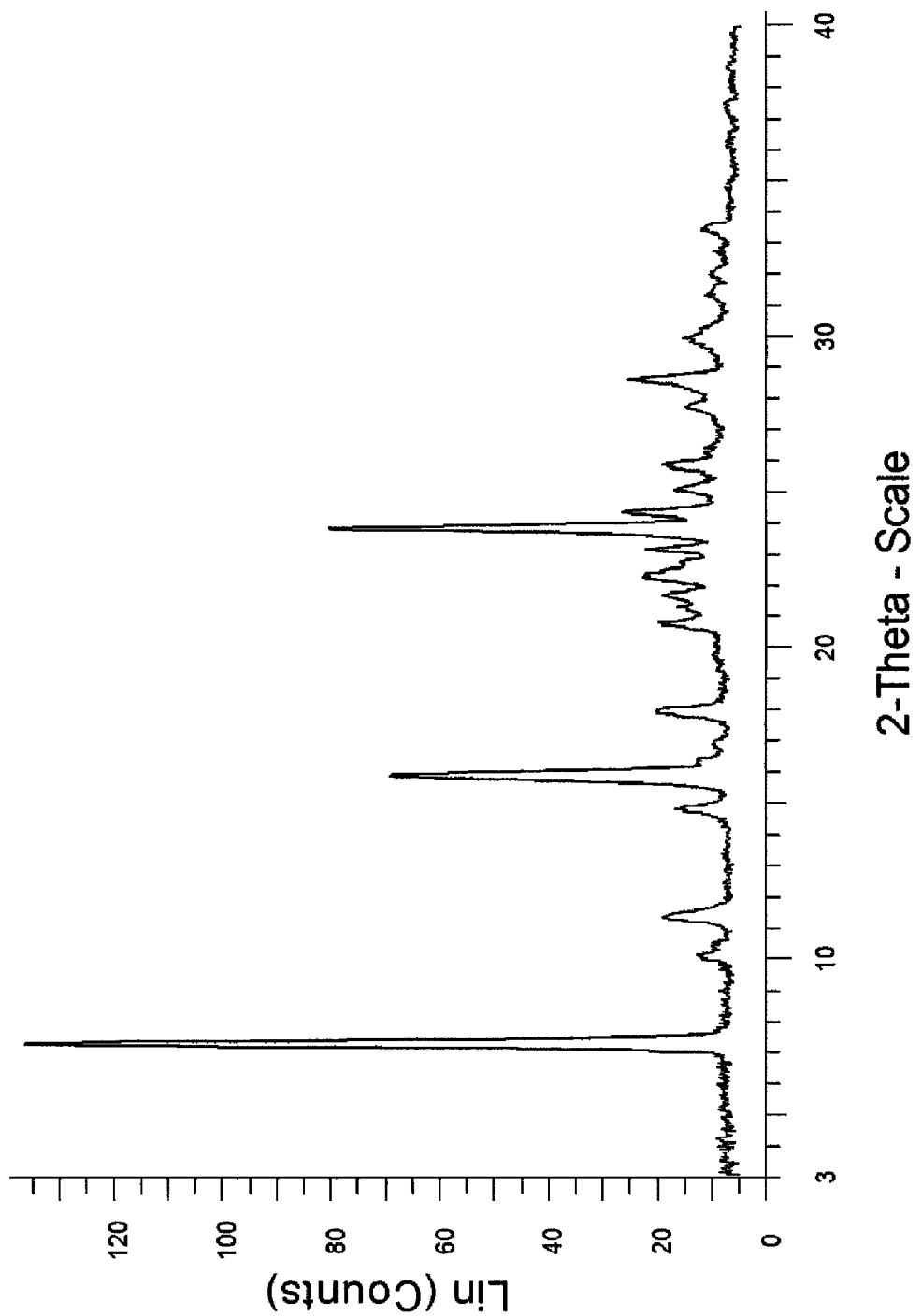

CRYSTAL OF AZOLE BENZENE DERIVATIVE

CROSS REFERENCE TO RELATED APPLICATIONS

This application is a National Stage of International Application No. PCT/JP2015/071512 filed Jul. 29, 2015, claiming priority based on Japanese Patent Application No. 2014-155031 filed Jul. 30, 2014, the contents of all of which are incorporated herein by reference in their entirety.

TECHNICAL FIELD

The present invention relates to a crystal of a novel azole benzene derivative useful as a therapeutic agent or a prophylactic agent for diseases associated with xanthine oxidase such as gout, hyperuricemia, tumor lysis syndrome, urinary calculi, hypertension, dyslipidemia, diabetes, cardiovascular diseases such as arteriosclerosis or heart failure, kidney diseases such as diabetic nephropathy, respiratory diseases such as chronic obstructive pulmonary diseases, inflammatory bowel diseases or autoimmune diseases.

BACKGROUND ART

Xanthine oxidase is an enzyme catalyzing the conversion of hypoxanthine to xanthine and further to uric acid in nucleic acid metabolism.

A xanthine oxidase inhibitor inhibits uric acid synthesis to reduce a level of uric acid in the blood with respect to the action of xanthine oxidase. That is, a xanthine oxidase inhibitor is effective as a therapeutic agent for hyperuricemia and various diseases caused by hyperuricemia. On the other hand, there are gouty arthritis and gouty tophus called gout as a clinical condition caused by a result of deposition of urate crystals after prolonged hyperuricemia. In addition, hyperuricemia is considered to be important as a factor of lifestyle diseases associated with obesity, hypertension, dyslipidemia and diabetes or metabolic syndromes, and recently, it has been clarified that hyperuricemia is a risk factor of renal damage, urinary calculi and cardiovascular diseases by epidemiological surveys (The Guideline Revising Committee of Japanese Society of Gout and Nucleic Acid Metabolism, ed., Guideline for the management of hyperuricemia and gout, second edition, Medical Review (2010)). In addition, a xanthine oxidase inhibitor is expected to be useful for the treatment of diseases associated with active oxygen species by inhibitory activity against the active oxygen species generation, for example, for the treatment of cardiovascular diseases through the vascular function-improving action (Circulation. 2006; 114: 2508-2516).

Allopurinol and febuxostat are clinically used as a therapeutic agent for hyperuricemia, but allopurinol has been reported to have a side effect such as Stevens-Johnson syndrome, toxic epidermal necrolysis, hepatic disorder and renal dysfunction (Nippon Rinsho, 2003; 61, Suppl. 1: 197-201).

As a compound having a xanthine oxidase inhibitory activity, for example, a 2-phenylthiazole derivative is reported (PTL 1 to 3).

On the other hand, in PTL 4 and 5, a dithiazole carboxylic acid derivative having a benzene ring in the center is reported. Further, in PTL 6 and 7, a biphenyl thiazole carboxylic acid derivative is reported.

CITATION LIST

Patent Literature

[PTL 1] International Publication No. 92/09279
[PTL 2] Japanese Patent Laid-Open No. 2002-105067
[PTL 3] International Publication No. 96/31211
[PTL 4] International Publication No. 2011/139886
[PTL 5] International Publication No. 2011/101867
[PTL 6] International Publication No. 2010/018458
[PTL 7] International Publication No. 2010/128163

SUMMARY OF INVENTION

Technical Problem

An object of the present invention is to provide a crystal of a novel compound useful as a therapeutic agent or a prophylactic agent for diseases associated with xanthine oxidase such as gout, hyperuricemia, tumor lysis syndrome, urinary calculi, hypertension, dyslipidemia, diabetes, cardiovascular diseases such as arteriosclerosis or heart failure, kidney diseases such as diabetic nephropathy, respiratory diseases such as chronic obstructive pulmonary diseases, inflammatory bowel diseases or autoimmune diseases.

Solution to Problem

As a result of earnest studies with the above object, the present inventors have found that 2-[4-(2,2-dimethylpropoxy)-3-(1H-1,2,3,4-tetrazol-1-yl)phenyl]-4-methyl-1,3-thiazole-5-carboxylic acid (hereinafter, also referred to as a compound (I)) can be crystallized and exists as at least one type of crystal polymorph.

That is, the present invention provides the following.

[1] A crystal of 2-[4-(2,2-dimethylpropoxy)-3-(1H-1,2,3,4-tetrazol-1-yl)phenyl]-4-methyl-1,3-thiazole-5-carboxylic acid;

[2] The crystal according to [1], wherein the crystal has a crystal form A;

[3] The crystal according to [2], wherein the crystal has characteristic peaks at diffraction angles of 2θ=7.2°, 11.3°, 15.9°, 17.9°, 20.8°, 22.3°, 23.1°, 23.8°, 24.3° and 28.6° in its powder X-ray diffraction spectrum;

[4] The crystal according to [2], wherein its powder X-ray diffraction spectrum has a pattern shown in FIG. 1;

[5] The crystal according to [2], wherein its exothermic peak in thermogravimetry/differential thermal analysis is at 232° C.;

[6] A pharmaceutical composition comprising the crystal according to any one of [1] to [5] and a pharmaceutically acceptable carrier;

[7] A xanthine oxidase inhibitor comprising the crystal according to any one of [1] to [5] as an active ingredient; and

[8] A therapeutic or prophylactic agent for one or more diseases selected from the group consisting of gout, hyperuricemia, tumor lysis syndrome, urinary calculi, hypertension, dyslipidemia, diabetes, cardiovascular diseases, kidney diseases, respiratory diseases, inflammatory bowel diseases and autoimmune diseases, comprising the crystal according to any one of [1] to [5] as an active ingredient.

Advantageous Effects of Invention

The present invention provides crystals of an azole benzene derivative, which are useful as therapeutic or prophylactic agents for diseases associated with xanthine oxidase such as gout, hyperuricemia, tumor lysis syndrome, urinary calculi, hypertension, dyslipidemia, diabetes, cardiovascular diseases such as arteriosclerosis or heart failure, kidney diseases such as diabetic nephropathy, respiratory diseases such as chronic obstructive pulmonary diseases, inflammatory bowel diseases or autoimmune diseases. These crystals can be used as an active pharmaceutical ingredient for producing pharmaceutical agent.

BRIEF DESCRIPTION OF DRAWINGS

FIG. 1 is a powder X-ray diffraction spectrum of crystal form A.

DESCRIPTION OF EMBODIMENTS

"Xanthine oxidase" is used both in a broad sense that it is an enzyme for catalyzing an oxidation reaction from hypoxanthine to xanthine and further to uric acid and in a narrow sense that it is an oxidase type xanthine oxidoreductase which is one of the enzymes that catalyze the same reaction. In the present invention, unless otherwise specified, "xanthine oxidase" is collectively called an enzyme which catalyzes an oxidation reaction from hypoxanthine to xanthine and further to uric acid. In the xanthine oxidoreductase which is responsible for this reaction, two types of oxidase type oxidoreductase and dehydrogenase type oxidoreductase are present and both types are included in the xanthine oxidase of the present invention. Unless otherwise specified, "xanthine oxidase" has the same meaning as defined above also in the "xanthine oxidase inhibitory activity", "xanthine oxidase inhibitor" and the like.

The crystals of the present invention are characterized by powder X-ray diffraction spectra, and/or thermogravimetry/differential thermal analysis (TG/DTA) and the like. The powder X-ray diffraction (XRD) spectra of these crystals exhibits characteristic patterns, and each crystal has specific diffraction angle 2θ values. In addition, each of these crystals also exhibits its own characteristic thermal behavior in thermogravimetry/differential thermal analysis (TG/DTA).

The crystal form A of the present invention has characteristic peaks at diffraction angles of 2θ=7.2°, 11.3°, 15.9°, 17.9°, 20.8°, 22.3°, 23.1°, 23.8°, 24.3° and 28.6° in its powder X-ray diffraction spectrum. In addition, the crystal form A of the present invention has a pattern in its powder X-ray diffraction spectrum shown in FIG. 1, and has an exothermic peak at 232° C. in the thermogravimetry/differential thermal analysis (TG/DTA). The crystal form A is an anhydrous crystal.

As used herein, "characteristic peaks" mean peaks which are mainly observed in the powder X-ray diffraction spectrum of each crystal polymorph, as well as unique peaks. The crystals of the present invention identified by the diffraction angles also include peaks other than those observed as the characteristic peaks described above.

The position and the relative intensity of diffraction angle 2θ in powder X-ray diffraction spectrum may slightly vary depending on the measurement conditions, and therefore, even if 2θ has a slight difference, the identity of a crystal form should be recognized by appropriately referring to the pattern of the entire spectrum. Crystals within the range of such errors are also included in the present invention. The errors in 2θ can be, for example, in the range of ±0.5° or ±0.2°. In other words, the crystals identified by the above diffraction angles also include those with diffraction angles within the error range of ±0.5° or ±0.2°.

In the thermogravimetric/differential thermal analysis (TG/DTA), an "exothermic peak" and an "endothermic peak" are defined as the temperature at the starting point of a peak and mean the exothermic and endothermic starting temperature determined by extrapolation. The "exothermic peak" and "endothermic peak" in the TG/DTA may vary a little depending on the measurement conditions. For example, the error is considered to be in the range of ±5° C. or ±2° C. In other words, the crystals identified by the above peaks also include those with peaks within the error range of ±5° C. or ±2° C.

Further, for both powder X-ray diffraction spectrum and TG/DTA, the difference between the measured values for a reference material of crystals, for example, each crystal obtained by the method described in the present examples and the numerical values described in the present application may be accepted as the measurement errors. That is, the crystals that have the same diffraction angles and exothermic and endothermic peaks within the range of errors calculated by such methods are included in the crystals of the present invention.

A crystal form A of 2-[4-(2,2-dimethylpropoxy)-3-(1H-1,2,3,4-tetrazol-1-yl)phenyl]-4-methyl-1,3-thiazole-5-carboxylic acid may be synthesized, for example, according to the synthesis method described below.

Synthesis of Compound (A-2)

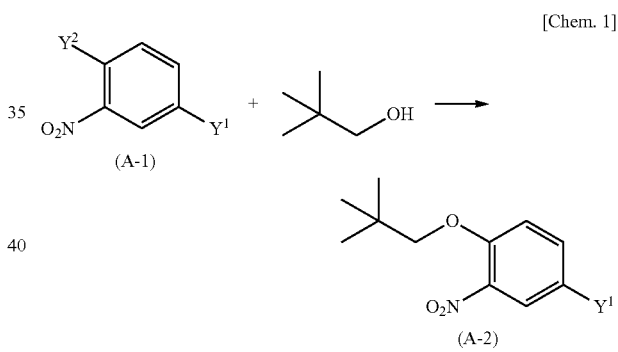

[Chem. 1]

(wherein Y¹ and Y² represent a leaving group.) Examples of a leaving group represented by Y¹ and Y² include a halogen atom, a methanesulfonyloxy group, a p-toluenesulfonyloxy group, a trifluoromethanesulfonyloxy group and the like. The reaction is a method for synthesizing a compound (A-2) by reaction of neopentyl alcohol with a leaving group Y² in a compound (A-1) in the presence of a base. Examples of the base to be used include an inorganic salt such as sodium hydride, sodium hydroxide, potassium hydroxide, lithium hydroxide, sodium carbonate, potassium carbonate, cesium carbonate; a metal alkoxide such as sodium ethoxide, sodium methoxide and potassium t-butoxide; and an organic amine such as triethylamine, pyridine, 4-aminopyridine, N-ethyl-N,N-diisopropylamine (DIPEA) and 1,8-diazabicyclo[5.4.0]-7-undecene (DBU). The reaction is performed by reacting a base in an equivalent or slightly excessive amount relative to the compound (A-1) and neopentyl alcohol in an equivalent or excessive amount relative to the compound (A-1) in a solvent inactive to the reaction in the range between 0° C. and 140° C., followed by adding the compound (A-1) to the mixture to allow the reaction to proceed generally for 0.5 to 16 hours. The reaction is preferably performed under an inert gas atmosphere such as nitrogen. Here, the solvent includes, though not particularly limited, for example, aromatic hydrocarbons such as benzene, toluene and xylene; ethers such as diethyl ether, tetrahydrofuran (THF), 1,4-dioxane, 1,2-dimethoxy ethane and 1,2-diethoxy ethane; halogenated hydrocarbons such as dichloromethane, 1,2-dichloroethane and chloroform; N,N-dimethylformamide (DMF); N-methylpyrrolidone; dimethyl sulfoxide (DMSO); water; or a mixed solvent thereof.

Synthesis of Compound (A-4)

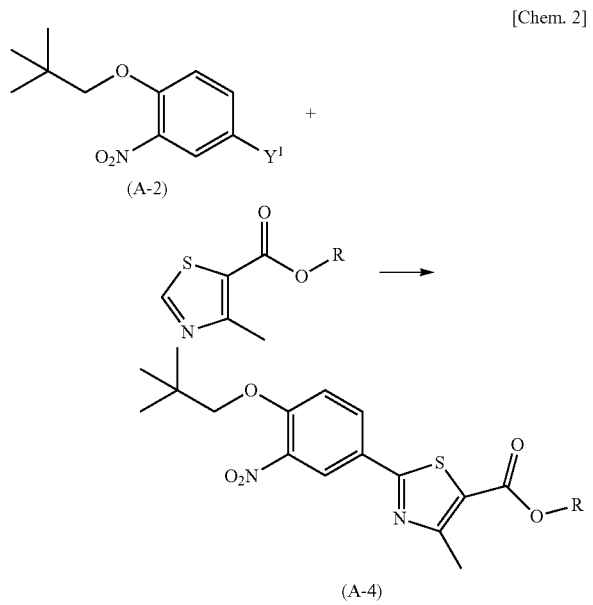

[Chem. 2]

(wherein R represents an alkyl group having 1 to 6 carbon atoms.) The synthesis method is a method for synthesizing a compound (A-4) by coupling compounds (A-2) and (A-3) together. Examples of a leaving group represented by $Y^1$ include a halogen atom, a methanesulfonyloxy group, a p-toluenesulfonyloxy group and a trifluoromethanesulfonyloxy group. The reaction is performed by reacting the compounds (A-2) and (A-3) using an equivalent or excessive amount of one compound relative to the other in a solvent inactive to the reaction in the presence of a base and a transition metal catalyst, adding a ligand, a carboxylic acid and a monovalent or divalent copper salt when necessary, in the range between room temperature and a reflux temperature generally for 0.5 hours to 2 days. The reaction is preferably performed under an inert gas atmosphere such as nitrogen. Here, the solvent includes, though not particularly limited, for example, aromatic hydrocarbons such as benzene, toluene and xylene; ethers such as diethyl ether, tetrahydrofuran (THF), 1,4-dioxane, 1,2-dimethoxy ethane and 1,2-diethoxy ethane; halogenated hydrocarbons such as dichloromethane, 1,2-dichloroethane and chloroform; alcohols such as methanol, ethanol, 2-propanol and butanol; N,N-dimethylformamide (DMF); N-methylpyrrolidone; dimethyl sulfoxide (DMSO); water; and a mixed solvent thereof. Examples of the base include lithium hydride, sodium hydride, potassium hydride, sodium hydroxide, potassium hydroxide, sodium carbonate, potassium carbonate, cesium carbonate, potassium fluoride, cesium fluoride, tripotassium phosphate, sodium acetate and potassium acetate; a metal salt of an alkoxide having 1 to 6 carbon atoms (lithium salt, sodium salt, potassium salt and magnesium salt); a metal salt of an alkyl anion having 1 to 6 carbon atoms (lithium salt, sodium salt, potassium salt and magnesium salt); tetra (alkyl having 1 to 4 carbon atoms) ammonium salt (fluoride, chloride and bromide); diisopropylethylamine; tributylamine; N-methylmorpholine; diazabicycloundecene; diazabicylcooctane; and imidazole. Examples of the transition metal catalyst include copper, palladium, cobalt, iron, rhodium, ruthenium and iridium. Examples of the ligand include tri(t-butyl)phosphine, tri (cyclohexyl)phosphine, t-butyldicyclohexylphosphine, di(t-butyl)cyclohexylphosphine and di(t-butyl)methylphosphine. Examples of the monovalent or divalent copper salt include copper chloride (I), copper bromide (I), copper iodide (I), copper acetate (I), copper fluoride (II), copper chloride (II), copper bromide (II), copper iodide (II), copper acetate (II), a hydrate thereof and a mixture thereof. Examples of the carboxylic acid include formic acid, acetic acid, propionic acid, n-butyric acid, isobutyric acid, pentanoic acid, isopentanoic acid, pivalic acid and trifluoroacetic acid.

Synthesis of Compound (A-5)

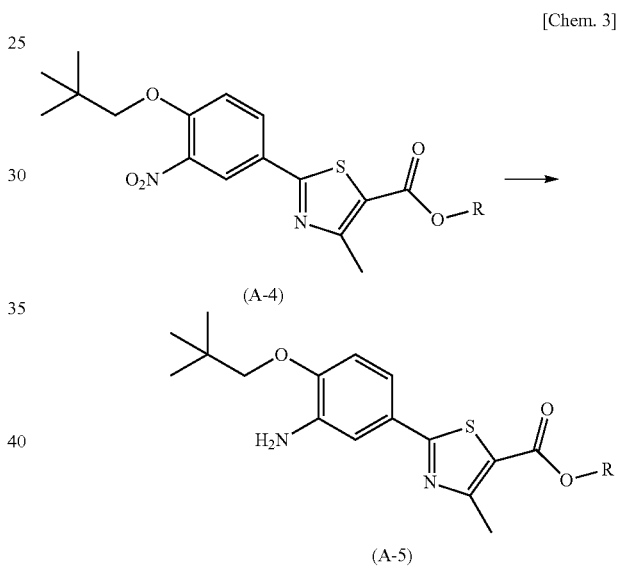

[Chem. 3]

(wherein R represents an alkyl group having 1 to 6 carbon atoms.) The synthesis method is a method for synthesizing a compound (A-5) by the reduction of a nitro group of the compound (A-4). The reaction is performed by reacting the compound (A-4) under a hydrogen gas atmosphere in a solvent inactive to the reaction in the presence of a transition metal catalyst in the range between room temperature and a reflux temperature generally for 0.5 hours to 2 days. Here, the solvent includes, though not particularly limited, for example, aromatic hydrocarbons such as benzene, toluene and xylene; ethers such as diethyl ether, tetrahydrofuran (THF), 1,4-dioxane, 1,2-dimethoxy ethane and 1,2-diethoxy ethane; halogenated hydrocarbons such as dichloromethane, 1,2-dichloroethane and chloroform; alcohols such as methanol, ethanol, 2-propanol and butanol; N,N-dimethylformamide (DMF); N-methylpyrrolidone; dimethyl sulfoxide (DMSO); ethyl acetate; and a mixed solvent thereof. Preferred examples of the transition metal catalyst include palladium-carbon, palladium hydroxide, palladium black, platinum-carbon, Raney nickel and the like.

Synthesis of Compound (A-6): an alkyl ester of 2-[4-(2,2-dimethylpropoxy)-3-(1H-1,2,3,4-tetrazol-1-yl)phenyl]-4-methyl-1,3-thiazole-5-carboxylic acid Synthesis of a crystal form A of Compound (I): 2-[4-(2,2-dimethylpropoxy)-3-(1H-1,2,3,4-tetrazol-1-yl)phenyl]-4-methyl-1,3-thiazole-5-carboxylic acid

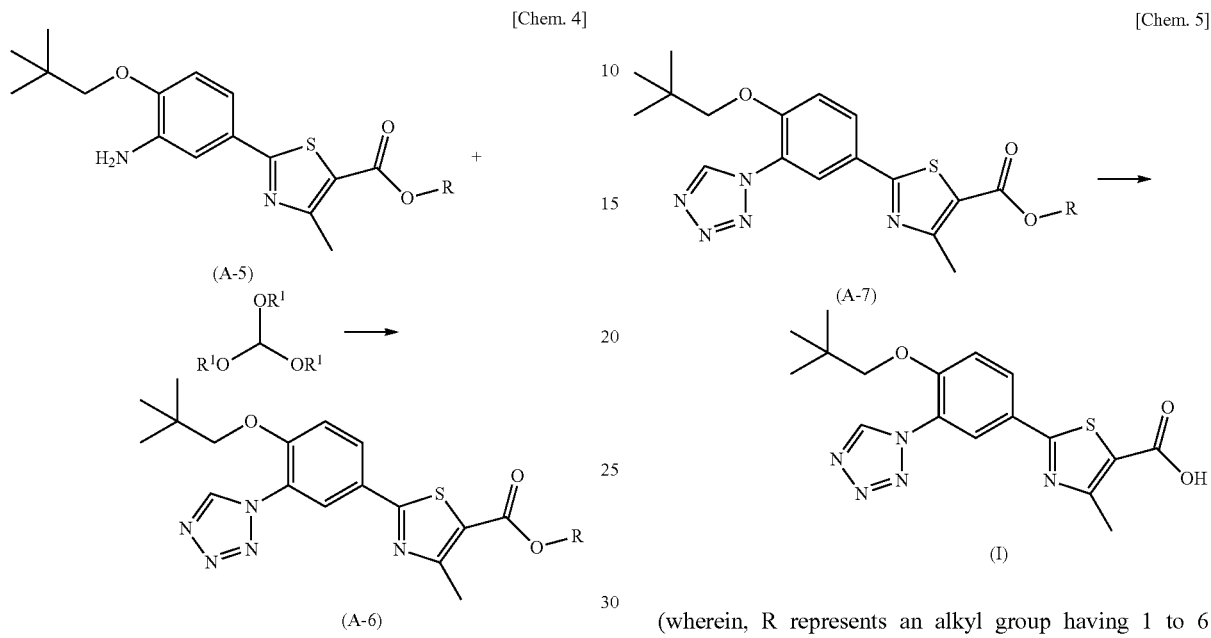

(wherein R and $R^1$ independently represent an alkyl group having 1 to 6 carbon atoms.) The synthesis method is a method for synthesizing a tetrazole ring by reacting the compound (A-5) with an orthoformate and an azide compound. The reaction is performed by reacting the compound (A-5), an orthoformate and an azide compound using an equivalent or excessive amount of one of the compounds in a solvent inactive to the reaction in the presence of an acid in the range between room temperature and a reflux temperature generally for 0.5 hours to 2 days. The reaction is preferably performed under an inert gas atmosphere such as nitrogen. Examples of the orthoformate include trimethyl orthoformate and triethyl orthoformate. In addition, examples of the azide compound include sodium azide and trimethyl silylazide. Examples of the acid to be used include an organic acid such as formic acid and acetic acid, an inorganic acid such as hydrochloric acid and sulfuric acid, and a Lewis acid such as indium triflate, ytterbium triflate, zinc triflate and trichloroindium. The solvent to be used for these reactions includes, though not particularly limited, for example, benzene, toluene, dichloromethane, dichloroethane, chloroform, carbon tetrachloride, diethyl ether, tetrahydrofuran (THF), 1,4-dioxane, 1,2-dimethoxy ethane, 1,2-diethoxy ethane, N,N-dimethylformamide (DMF), N-methylpyrrolidone, dimethyl sulfoxide (DMSO) and a mixed solvent thereof, and an acid such as acetic acid may also be used as a solvent.

(wherein, R represents an alkyl group having 1 to 6 carbon atoms.) A crystal form A of the compound (I) can be produced by a method comprising a step of suspending a compound (A-7) in a solvent and hydrolyzing the suspension by adding an aqueous solution of a base and a step of neutralizing the reaction product. In addition, the method may further comprise a step of adding water to the neutralized product and a subsequent step of stirring the reaction solution. The solvent used for suspending compound (A-7) includes, for example, aromatic hydrocarbons such as benzene, toluene and xylene; ethers such as diethyl ether, tetrahydrofuran (THF), 1,4-dioxane, 1,2-dimethoxy ethane and 1,2-diethoxy ethane; halogenated hydrocarbons such as dichloromethane, 1,2-dichloroethane and chloroform; alcohols such as methanol, ethanol, 2-propanol and butanol; N,N-dimethylformamide (DMF); N-methylpyrrolidone; dimethyl sulfoxide (DMSO); water; and a mixed solvent thereof. The solvent preferably is an ether, an alcohol, water or a mixed solvent thereof.

In the compound (A-7), R preferably is an alkyl group having 1 to 6 carbon atoms and more preferably an ethyl group. Here, an alkyl group is referred to as a linear or branched aliphatic saturated hydrocarbon group. Specific examples of an alkyl group having 1 to 6 carbon atoms include a methyl group, an ethyl group, a propyl group, an isopropyl group, a butyl group, an isobutyl group, a tert-butyl group, a pentyl group, an isopentyl group and a hexyl group.

The hydrolysis reaction from the compound (A-7) to the compound (I) proceeds by suspending the compound (A-7) in the solvent (for example, in an amount of 15 times the amount of the compound (A-7)) and then reacting the compound (A-7) with a base in an equivalent or slightly excessive amount relative to the compound (A-7). Examples of preferred bases include sodium hydroxide, potassium hydroxide and lithium hydroxide. The reaction proceeds in the range between 0° C. and 100° C. but is performed preferably in the range between 20° C. and 30° C. After the hydrolysis reaction, the reaction product is neutralized by reacting the base used with an acid in an equivalent or slightly excessive amount relative to the base used. An example of a preferred acid includes hydrochloric acid. The neutralization reaction proceeds in the range between 0° C. and 100° C. but is performed preferably in the range between 0° C. to 30° C.

Subsequently, water (for example, in an amount of 5 times the amount of the compound (A-7)) is added to the neutralized reaction product and the mixture is stirred for one hour, and then the precipitate is filtered out and dried to obtain crystals. Although the amount of the solvent, the amount of water added, stirring conditions and the time until separation by filtering are not particularly limited, since these conditions may have an influence on the yield of crystals, chemical purity, particles diameter and particle size distribution, these conditions are preferably combined and set according to the purpose. For the filtration, a usual method, for example, natural filtration, pressure filtration, vacuum filtration, or centrifuge separation can be used. For the drying, a usual method, for example, natural drying, vacuum drying, heating drying and vacuum heating drying can be used. The intermediate compound of the reaction can be purified by a usual method such as recrystallization, reprecipitation and various chromatography methods, if necessary, during the synthesis process.

Although the crystals of the present invention can be identified by a characteristic powder X-ray diffraction spectrum or thermogravimetric/differential thermal analysis (TG/DTA), when other crystal forms are present, the incorporation rate thereof is not referred to. When only a specific form of crystal is obtained, at least the incorporation of the other crystal forms may be accepted to a degree that cannot be detected by these methods of measurement. In addition, when a specific form of crystal is used as an active pharmaceutical ingredient for a pharmaceutical agent, it does not mean that the inclusion of the other forms of crystals is unacceptable.

The crystals of the present invention can be used as a pharmaceutical active ingredient. In addition, when the other crystal forms are present, not only one form of crystals but also a mixture of two or more forms of crystals can be used. In the present invention, the handleability during production, reproducibility, stability and storage stability are made advantageous by obtaining crystals of 2-[4-(2,2-dimethylpropoxy)-3-(1H-1,2,3,4-tetrazol-1-yl)phenyl]-4-methyl-1,3-thiazole-5-carboxylic acid compared with those that are not crystalline.

A pharmaceutical composition can be obtained by using the crystals of the present invention and a pharmaceutically acceptable carrier.

A preparation containing the crystals of the present invention is prepared using additives usually used for formulation. Examples of the additives for a solid preparation include an excipient such as lactose, saccharose, glucose, corn starch, white potato starch, crystalline cellulose, light anhydrous silicic acid, synthetic aluminum silicate, magnesium aluminometasilicate and calcium hydrogen phosphate; a binder such as crystalline cellulose, carboxymethyl cellulose, hydroxypropyl cellulose, carboxymethylcellulose sodium and polyvinyl pyrrolidone; a disintegrating agent such as starch, carboxymethylcellulose sodium, carboxymethylcellulose calcium, croscarmellose sodium and sodium carboxy methyl starch; a lubricant such as talc and stearic acid; a coating agent such as hydroxymethylpropylcellulose, hydroxypropylmethylcellulose phthalate and ethylcellulose; and a coloring agent, the additives for a semisolid preparation include a base such as white petrolatum, and the additives for a liquid preparation include a solvent such as ethanol; a solubilizing agent such as ethanol; a preservative such as para-hydroxybenzoate; a tonicity agent such as glucose; a buffering agent such as citric acid; an antioxidant such as L-ascorbic acid; a chelating agent such as EDTA; and a suspending agent and an emulsifying agent such as polysorbate 80.

The crystals of the present invention can be used in any dosage forms such as a solid preparation, a semisolid preparation and a liquid preparation, and used in a preparation for any form of administration such as an oral preparation and a parenteral preparation (such as an injection preparation, a percutaneous preparation, an ophthalmic preparation, a suppository preparation, a transnasal preparation and an inhalation preparation).

A pharmaceutical composition containing the crystals of the present invention as an active ingredient can be used as a xanthine oxydase inhibitor or a therapeutic agent and a prophylactic agent for diseases associated with xanthine oxidase such as gout, hyperuricemia, tumor lysis syndrome, urinary calculi, hypertension, dyslipidemia, diabetes, cardiovascular diseases such as arterialsclerosis and heart failure, kidney diseases such as diabetic nephropathy, respiratory diseases such as chronic obstructive pulmonary disease, inflammatory bowel diseases or autoimmune diseases. Here, the term "prophylactic" means to prevent the incidence or onset of diseases in an individual who is not affected by diseases or has not yet developed diseases and the term "therapeutic" means to treat, suppress or remedy diseases or symptoms in an individual who has already been affected by diseases or has developed diseases.

EXAMPLES

[Measurement Method]

The powder X-ray diffraction of the crystals of the present invention was measured under the following conditions.

Apparatus: D8 DISCOVER with GADDS CS manufactured by Bruker AXS

Radiation source: Cu Kα, Wavelength: 1.541838 ($10^{-10}$ m), 40 kV-40 mA, Incident flat plate graphite monochromator, collimator diameter 300 μm, two-dimensional PSPC detector, scan 3 to 40°

The thermogravimetric/differential thermal analysis (TG/DTA) of the crystals of the present invention was measured under the following conditions.

Apparatus: TG8120 manufactured by Rigaku

Temperature elevation rate: 10° C./min, Atmosphere: nitrogen, Sample pan: aluminum, Reference: alumina, Sampling: 1.0 sec., Measurement temperature range: 25 to 300° C.

As for the compounds for which $^1$H-NMR spectrum (400 MHz, DMSO-$d_6$ or CDCl$_3$) was measured, the chemical shift (δ: ppm) and coupling constant (J: Hz) are shown.

Apparatus: JMTC-400/54/SS manufactured by JEOL

The abbreviations represent the followings:

s=singlet, d=doublet, t=triplet, q=quartet, brs=broad singlet, m=multiplet

Reference Example 1

Production of ethyl 2-[4-(2,2-dimethylpropoxy)-3-(1H-1,2,3,4-tetrazol-1-yl)phenyl]-4-methyl-1,3-thiazole-5-carboxylate (1) A mixture prepared by suspending 1.06 g of neopentyl alcohol in 40.0 mL of toluene was cooled to 0° C. under a nitrogen atmosphere, and 1.35 g of t-butoxysodium was added and the resultant mixture was stirred at 0° C. for 30 minutes. Subsequently, after adding 2.20 g of 4-bromo-1-fluoro-2-nitrobenzene to the above mixture at 0° C., the resultant reaction mixture solution was warmed to room temperature and stirred at room temperature for 2 hours. After the addition of water to the reaction mixture solution, extraction was performed using ethyl acetate. The organic layer was washed with a saline solution, followed by drying and concentration under reduced pressure to obtain 3.12 g of 4-bromo-1-(2,2-dimethylpropoxy)-2-nitrobenzene.

(2) A suspension was prepared by adding 3.04 g of potassium bicarbonate, 63 mg of palladium chloride (II) and 297 mg of copper bromide (I) to 4.18 g of 4-bromo-1-(2,2-dimethylpropoxy)-2-nitrobenzene, and suspending the mixture in 45 mL of toluene. Subsequently, a reaction mixture solution prepared by adding 2.97 g of ethyl 4-methyl-1,3-thiazole-5-carboxylate, 133 µL of isobutyric acid and 333 µL of di-t-butylcyclohexylphosphine to the suspension was heated at 120° C. for 14 hours under a nitrogen atmosphere. The reaction mixture solution was celite-filtered to remove insoluble matter, water was added to the filtrate, and extraction was performed using ethyl acetate. The organic layer was washed with a saline solution and then subjected to drying and concentration under reduced pressure, followed by purifying by a conventional method to obtain 5.13 g of ethyl 2-[4-(2,2-dimethylpropoxy)-3-nitrophenyl]-4-methyl-1,3-thiazole-5-carboxylate.

$^1$H-NMR (400 Mz, CDCl3) δ: 1.08 (9H, s), 1.39 (3H, t, J=6.8 Hz), 2.77 (3H, s), 3.79 (2H, s), 4.36 (2H, q, J=6.8 Hz), 7.12 (1H, d, J=8.8 Hz), 8.10 (1H, dd, J=2.0, 8.8 Hz), 8.45 (1H, d, J=2.0 Hz)

(3) A reaction mixture solution was prepared by suspending 5.13 g of ethyl 2-[4-(2,2-dimethylpropoxy)-3-nitrophenyl]-4-methyl-1,3-thiazole-5-carboxylate in 50 mL of ethanol, and adding 500 mg of palladium/carbon (10% wt) to the suspension, and the reaction mixture was stirred at 50° C. for 20 hours under a hydrogen atmosphere. The reaction mixture solution was filtered and the filtrate was concentrated under reduced pressure to obtain 4.66 g of ethyl 2-[3-amino-4-(2,2-dimethylpropoxy)phenyl]-4-methyl-1,3-thiazole-5-carboxylate.

(4) A reaction mixture solution prepared by suspending 2.58 g of ethyl 2-[3-amino-4-(2,2-dimethylproxy)phenyl]-4-methyl-1,3-thiazole-5-carboxylate in 30 mL of acetic acid and adding 962 mg of sodium azide and 2.19 g of triethyl orthoformate was heated at 70° C. for 2 hours under a nitrogen atmosphere. After cooling the reaction mixture to room temperature, 20 mL of water was added, followed by purifying by a conventional method to obtain 2.78 g of ethyl 2-[4-(2,2-dimethylpropoxy)-3-(1H-1,2,3,4-tetrazol-1-yl)phenyl]-4-methyl-1,3-thiazole-5-carboxylate.

$^1$H-NMR (400 Mz, CDCl3) δ: 1.00 (9H, s), 1.39 (3H, t, J=6.8 Hz), 2.78 (3H, s), 3.82 (2H, s), 4.36 (2H, q, J=6.8 Hz), 7.18 (1H, d, J=8.8 Hz), 8.08 (1H, dd, J=2.4, 8.8 Hz), 8.42 (1H, d, J=2.4 Hz), 9.19 (1H, s)

Example 1

Production of a crystal form A of 2-[4-(2,2-dimethylpropoxy)-3-(1H-1,2,3,4-tetrazol-1-yl)phenyl]-4-methyl-1,3-thiazole-5-carboxylic acid A reaction mixture solution prepared by dissolving 2.58 g of ethyl 2-[4-(2,2-dimethylpropoxy)-3-(1H-1,2,3,4-tetrazol-1-yl)phenyl]-4-methyl-1,3-thiazole-5-carboxylate in 30.0 L of a mixed solution of tetrahydrofuran/methanol=1/1 followed by the addition of 6.50 mL of 2 M sodium hydroxide aqueous solution was stirred in the range between 20° C. and 30° C. for 3 hours. While stirring in the range between 20° C. and 30° C., 6.50 mL of 2 M hydrochloric acid is slowly added to the reaction mixture solution and further 17.0 mL of water was slowly added. The reaction mixture solution was stirred in the range between 20° C. and 30° C. for one hour and crystals were obtained by filtration. The resulting crystals were washed with 7.0 mL of a mixed solution of methanol/water=1/1 and 7.0 mL of water. The crystals were vacuum dried at 50° C. to yield 2.25 g of crystals of 2-[4-(2,2-dimethylpropoxy)-3-(1H-1,2,3,4-tetrazol-1-yl)phenyl]-4-methyl-1,3-thiazole-5-carboxylic acid. The XRD of the resultant crystals is shown in FIG. 1. Peaks were observed at diffraction angles of 2θ=7.2°, 11.3°, 15.9°, 17.9°, 20.8°, 22.3°, 23.1°, 23.8°, 24.3° and 28.6°. In addition, an exothermic peak in thermogravimetry/differential thermal analysis (TG/DTA) was observed at 232° C.

$^1$H-NMR (400 Mz, DMSO-d6) δ: 0.83 (9H, s), 2.66 (3H, s), 3.83 (2H, s), 7.47 (1H, d, J=8.8 Hz), 8.18 (1H, dd, J=2.4, 8.8 Hz), 8.27 (1H, d, J=2.0 Hz), 9.78 (1H, s), 13.40 (1H, s)

Reference Example 2

Production of 2-[4-(2,2-dimethylpropoxy)-3-(1H-1,2,3,4-tetrazol-1-yl)phenyl]-4-methyl-1,3-thiazole-5-carboxylic acid A reaction mixture solution prepared by dissolving 307 mg of ethyl 2-[4-(2,2-dimethylpropoxy)-3-(1H-1,2,3,4-tetrazol-1-yl)phenyl]-4-methyl-1,3-thiazole-5-carboxylate in 8.0 mL of a mixed solution of tetrahydrofuran/methanol=1/1 followed by the addition of 1.0 mL of 2 M sodium hydroxide aqueous solution was stirred at room temperature for 3 hours. After adding 1.0 mL of 2 M hydrochloric acid to the reaction mixture solution, 6.0 mL of water was added, followed by purifying by a conventional method to obtain 244 mg of 2-[4-(2,2-dimethylpropoxy)-3-(1H-1,2,3,4-tetrazol-1-yl)phenyl]-4-methyl-1,3-thiazole-5-carboxylic acid.

$^1$H-NMR (DMSO-d6) δ: 0.83 (9H, s), 2.66 (3H, s), 3.83 (2H, s), 7.47 (1H, d, J=8.8 Hz), 8.18 (1H, dd, J=2.4, 8.8 Hz), 8.27 (1H, d, J=2.0 Hz), 9.78 (1H, s), 13.40 (1H, s)

Reference Example 3

Measurement of Xanthine Oxidase Inhibitory Activity (1) Preparation of Test Compound After dissolving 2-[4-(2,2-dimethylpropoxy)-3-(1H-1,2,3,4-tetrazol-1-yl)phenyl]-4-methyl-1,3-thiazole-5-carboxylic acid in DMSO (produced by Sigma Corporation) so that the concentration is 20 mM, the solution was used by adjusting the concentration to a desired value for the purpose during use.

(2) Measurement Method

The evaluation of the xanthine oxidase inhibitory activity of 2-[4-(2,2-dimethylpropoxy)-3-(1H-1,2,3,4-tetrazol-1-yl) phenyl]-4-methyl-1,3-thiazole-5-carboxylic acid was conducted by the method described in the refference (Method Enzymatic Analysis, 1, 521-522, 1974) with partial modification. This evaluation was carried out by measuring oxidase-type xanthine oxidoreductase acrivity. Concretely, a xanthine (manufactured by Sigma Co.) solution was prepared at 10 mM using a 20 mM sodium hydroxide solution and then mixed with 100 mM phosphate buffer to adjusted to 30 µM. 75 µL of the solution was added to each well of the 96-well plate. The test compound diluted with DMSO at 100 times of a final concentration was added to each well at 1.5 μL per well. After mixing the plate, absorbance at 290 nm was measured by a microplate reader SPECTRA MAX Plus 384 (manufactured by Molecular Devices, LLC). Subsequently, oxidase-type xanthine oxidoreductase (from buttermilk, manufactured by Calbiochem Novabiochem Corp.) was prepared at 30.6 mU/mL using a 100 mM phosphate buffer solution and added to each well at 73.5 μL per well. Immediately after mixing, the change of absorbance at 290 nm was measured for 5 minutes. The enzyme activity of DMSO solution without test compound was used as 100% control, and the inhibitory rate of the test compound was calculated. Fifty percent inhibitory concentration of the test compound on the oxidase-type xanthine oxidoreductase activity was calculated by fitting to the dose-response curve.

2-[4-(2,2-dimethylpropoxy)-3-(1H-1,2,3,4-tetrazol-1-yl)phenyl]-4-methyl-1,3-thiazole-5-carboxylic acid showed a xanthine oxidase inhibitory activity of $1.0\ nM \leq IC_{50} < 5.0\ nM$.

Reference Example 4

Hypouricemic Effect (Normal Rats)

The hypouricemic effect was confirmed for 2-[4-(2,2-dimethylpropoxy)-3-(1H-1,2,3,4-tetrazol-1-yl)phenyl]-4-methyl-1,3-thiazole-5-carboxylic acid. A test compound suspended in a 0.5% methylcellulose solution was forcibly administered to 8 to 9 week-old Sprague-Dawley male rats (Japan Charles River Co.) by oral gavage administration using a feeding needle. After the blood was collected from the tail vein at 2 hours after administration, the plasma was separated. The level of uric acid in the blood sample was measured by uricase method using an absorption spectrometer as well as a uric acid determination kit (L type Wako UA F: Wako Pure Chemical Industries, Ltd.). The percentage of hypouricemic effect was determined by the following expression:

Percentage of hypouricemic effect (%)=(Level of uric acid of the control animal−Level of uric acid of the test compound-administered animal)×100/Level of uric acid of the control animal.

2-[4-(2,2-dimethylpropoxy)-3-(1H-1,2,3,4-tetrazol-1-yl)phenyl]-4-methyl-1,3-thiazole-5-carboxylic acid showed a hypouricemic effect of 50% or more in both doses of 10 mg/kg and 1 mg/kg.

From the above results, it was shown that 2-[4-(2,2-dimethylpropoxy)-3-(1H-1,2,3,4-tetrazol-1-yl)phenyl]-4-methyl-1,3-thiazole-5-carboxylic acid has a potent hypouricemic effect.

Reference Example 5

Prolonged Hypouricemic Effect (Normal Rats)

2-[4-(2,2-dimethylpropoxy)-3-(1H-1,2,3,4-tetrazol-1-yl)phenyl]-4-methyl-1,3-thiazole-5-carboxylic acid was administered to Sprague-Dawley male rats in the same manner as in Reference Example 4. After the blood was collected from the tail vein 24 hours after administration, the plasma was separated. The level of uric acid in the blood was measured by an uricase method using an absorption spectrometer and a uric acid determination kit (L type Wako UA F: Wako Pure Chemical Industries, Ltd.). The percentage of hypouricemic effect was determined by the following expression:

Percentage of hypouricemic effect (%)=(Level of uric acid of the control animal−Level of uric acid of the test compound-administered animal)×100/Level of uric acid of the control animal.

2-[4-(2,2-dimethylpropoxy)-3-(1H-1,2,3,4-tetrazol-1-yl)phenyl]-4-methyl-1,3-thiazole-5-carboxylic acid showed a hypouricemic effect of 50% or more in a dose of 10 mg/kg and 40% or more in a dose of 3 mg/kg at 24 hours after administration.

From the above results, it was shown that 2-[4-(2,2-dimethylpropoxy)-3-(1H-1,2,3,4-tetrazol-1-yl)phenyl]-4-methyl-1,3-thiazole-5-carboxylic acid has a prolonged hypouricemic effect over a long period of time.

Reference Example 6

Hypouricemic Effect (Hyperuricemic Beagle Dogs)

The hypouricemic effect of 2-[4-(2,2-dimethylpropoxy)-3-(1H-1,2,3,4-tetrazol-1-yl)phenyl]-4-methyl-1,3-thiazole-5-carboxylic acid in oxonic acid-induced hyperuricmic beagle dog was confirmed. A test compound suspended in a 0.5% methylcellulose solution was administered to beagle dog (Kitayama labes) by oral gavage administration. Potassium oxonate (50 mg/kg) was subcutaneously administrated before and 4 hours after compound administration. After the blood was collected from the cephalic vein at 8 hours after administration, the plasma was separated. The level of uric acid in the plasma sample was measured by LC-MS/MS method and the percentage of hypouricemic effect was determined by the following expression:

Percentage of hypouricemic effect (%)=(Level of uric acid of the control animal−Level of uric acid of the test compound-administered animal)×100/Level of uric acid of the control animal.

2-[4-(2,2-dimethylpropoxy)-3-(1H-1,2,3,4-tetrazol-1-yl)phenyl]-4-methyl-1,3-thiazole-5-carboxylic acid showed a hypouricemic effect of 80% or more in a dose of 10 mg/kg at 8 hours after administration.

From the above results, it was shown that the compounds of the present invention have a potent hypouricemic effect in beagle dog.

Reference Example 7

Prolonged inhibitory effect of xanthine oxidase in tissue and plasma.

For "xanthine oxidase" in the present invention, as far as this example, oxidative reaction catalyzing activities which are brought by oxidase-type xanthine oxidoreductase solely and by both oxidase-type and dehydrogenase-type xanthine oxidoreductase are distinguished. The former is "XO activity" and the latter is "XOR activity". In "tissue XO activity", "plasma XO activity", "tissue XOR activity inhibition", "tissue XOR activity inhibition" and the like, "XO activity" and "XOR activity" have the same meanings as defined above. The tissue includes liver, kidney and vessel. In addition, percentage of XO activity inhibition and that of XO activity inhibition in same sample are thought to be similar, according to the results below.

The inhibitory effect of tissue XO activity, tissue XOR activity and plasma XO activity was confirmed for 2-[4-(2,2-dimethylpropoxy)-3-(1H-1,2,3,4-tetrazol-1-yl)phenyl]-4-methyl-1,3-thiazole-5-carboxylic acid. A test compound suspended in a 0.5% methylcellulose solution was forcedly administered to 7 to 9 week-old Sprague-Dawley male rats (Japan Charles River Co.) by oral gavage administration using a feeding needle. The blood was collected from the abdominal vein and tissue was collected at 24 or 27 hours after administration. Plasma sample was prepared by centrifugation.

The tissue XO activity, the tissue XOR activity and the plasma XO activity were measured by the pterin-based assay which utilizes the reaction that pterin is oxidized by each type of xanthine oxidoreductase to produce fluorescent isoxanthopterin. In brief, frozen tissues were homogenized with potassium phosphate buffer, pH 7.4, containing 1 mM ethylenediaminetetraacetic acid (EDTA) and protease inhibitors to prepare tissue concentration as follow (liver: 25 mg/mL, kidney: 25 mg/mL, vessel: 30 mg/mL). Then the homogenates were centrifuged 12,000 rpm for 15 min at 4° C. When measured XO activity, the supernatant of tissue and plasma were respectively co-incubated with 50 μM pterin solution at 37° C. When measured XOR activity, the supernatant of tissue homogenate was co-incubated with 50 μM pterin and 50 μM methylene blue solution at 37° C. As a control, oxidase-type xanthine oxidoreductase (from buttermilk, manufactured by Calbiochem Novabiochem Corp.) was also incubated with pterin solution in the same manner. XO activity and XOR activity of the samples were determined from fluorescence intensity which normalized by the intensity value of control and protein concentration.

The percentage of XO activity inhibition and XOR activity inhibition were determined by the following expression:

Percentage of XO or XOR activity inhibition (%)=
(XO or XOR activity of the control animal−XO or XOR activity of the test compound-administered animal)×100/XO or XOR activity of the control animal.

Liver and kidney XO activities and plasma XO activity 27 hours after administration are shown in the table below.

TABLE 1

| XO inhibitory activity of tissue and plasma (at the dissection about 27 hours after administration) % of inhibition (vs. vehicle) | | |
|---|---|---|
| Dose (mg/kg) | 1 | 10 |
| Liver | ≥80% | ≥80% |
| Kidney | ≥60% | ≥70% |
| Plasma | ≥25% | ≥40% |

2-[4-(2,2-dimethylpropoxy)-3-(1H-1,2,3,4-tetrazol-1-yl)phenyl]-4-methyl-1,3-thiazole-5-carboxylic acid inhibited 80% or more XO activity 27 hours after drug administration compared to the control animal at the dose of 10 mg/kg in liver.

The present compound inhibited 70% or more XO activity 27 hours after drug administration compared to the control animal at the dose of 10 mg/kg in kidney.

The present compound inhibited 40% or more XO activity 27 hours after drug administration compared to the control animal at the dose of 10 mg/kg in plasma.

The present compound inhibited 80% or more XOR activity 27 hours after drug administration compared to the control animal at the dose of 1 mg/kg in liver.

The present compound inhibited 60% or more XOR activity 27 hours after drug administration compared to the control animal at the dose of 1 mg/kg in kidney.

The present compound inhibited 25% or more XO activity 27 hours after drug administration compared to the control animal at the dose of 1 mg/kg in plasma.

In addition, the vessel XOR inhibitory activity at 24 hours after administration is shown in the following table.

TABLE 2

| XOR inhibitory activity of tissue (at the dissection 24 hours after administration) % of inhibition (vs. vehicle) | | |
|---|---|---|
| Dose (mg/kg) | 1 | 10 |
| Liver | ≥80% | ≥80% |
| Vessel | ≥30% | ≥50% |

2-[4-(2,2-dimethylpropoxy)-3-(1H-1,2,3,4-tetrazol-1-yl)phenyl]-4-methyl-1,3-thiazole-5-carboxylic acid inhibited 80% or more XOR activity 24 hours after drug administration compared to the control animal at the dose of 10 mg/kg in liver.

The present compound inhibited 50% or more XOR activity 24 hours after drug administration compared to the control animal at the dose of 10 mg/kg in vessel.

Further, the present compound inhibited 80% or more XOR activity 24 hours after drug administration compared to the control animal at the dose of 1 mg/kg in liver.

The present compound inhibited 30% or more XOR activity 24 hours after drug administration compared to the control animal at the dose of 1 mg/kg in vessel.

From the above results, it was shown that the compound of the present invention has a prolonged inhibitory effect of XO activity or XOR activity.

INDUSTRIAL APPLICABILITY

The crystals of 2-[4-(2,2-dimethylpropoxy)-3-(1H-1,2,3,4-tetrazol-1-yl)phenyl]-4-methyl-1,3-thiazole-5-carboxylic acid of the present invention are used as a pharmaceutical agent. Furthermore, these crystals can be used as an active pharmaceutical ingredient for producing a pharmaceutical agent.

The invention claimed is:

1. A crystal form A of 2-[4-(2,2-dimethylpropoxy)-3-(1H-1,2,3,4-tetrazol-1-yl)phenyl]-4-methyl-1,3-thiazole-5-carboxylic acid, wherein the crystal has characteristic peaks at diffraction angles of 2θ=7.2°, 11.3°, 15.9°, 17.9°, 20.8°, 22.3°, 23.1°, 23.8°, 24.3° and 28.6° in its powder X-ray diffraction spectrum.

2. The crystal according to claim 1, wherein its powder X-ray diffraction spectrum has a pattern shown in FIG. 1.

3. The crystal according to claim 1, wherein its exothermic peak in thermogravimetry/differential thermal analysis is at 232° C.

4. A pharmaceutical composition comprising the crystal according to claim 1 and a pharmaceutically acceptable carrier.

* * * * *